United States Patent [19]

Costello

[11] Patent Number: 4,682,895
[45] Date of Patent: Jul. 28, 1987

[54] FIBER OPTIC PROBE FOR QUANTIFICATION OF COLORIMETRIC REACTIONS

[75] Inventor: David Costello, College Station, Tex.

[73] Assignee: Texas A&M University, College Station, Tex.

[21] Appl. No.: 763,019

[22] Filed: Aug. 6, 1985

[51] Int. Cl.$^4$ ............................................. G01J 3/50
[52] U.S. Cl. .................... 356/402; 350/96.29; 128/634; 128/636; 250/227; 356/409; 356/440; 422/58; 422/68; 436/164
[58] Field of Search ............ 356/39, 40, 41, 402, 356/409, 410, 436, 440; 128/633, 634, 637, 636; 350/96.15, 96.29; 250/227; 422/58, 68; 436/164

[56] References Cited

U.S. PATENT DOCUMENTS

| | | | |
|---|---|---|---|
| 3,068,742 | 12/1962 | Hicks et al. | 356/41 |
| 3,123,066 | 3/1964 | Brumley | 128/2 |
| 3,814,081 | 6/1974 | Mori | 356/41 |
| 4,200,110 | 4/1980 | Peterson et al. | 128/634 |
| 4,306,877 | 12/1981 | Lubbers | 436/166 |
| 4,344,438 | 8/1982 | Schultz | 128/634 |
| 4,369,364 | 1/1983 | Kuntermann | 250/227 |
| 4,497,577 | 2/1985 | Sato et al. | 356/336 |

FOREIGN PATENT DOCUMENTS

| | | | |
|---|---|---|---|
| 0073558 | 6/1982 | European Pat. Off. | |
| 0126600 | 11/1984 | European Pat. Off. | 356/402 |
| 53-110848 | 3/1980 | Japan | |
| 0124036 | 9/1981 | Japan | 356/39 |
| 0154340 | 9/1984 | Japan | 356/436 |

OTHER PUBLICATIONS

"Designing with DuPont CROFON Fiber Optics", DuPont Co. Brochure.
"Fiber Optic pH Probe for Physiological Use", Peterson, et al. *Anal. Chem.* 52, 1980, pp. 864–869.
"A Miniature Fiber Optic pH Sensor for Physiological Use", Goldstein, et al., Journal of Biomechanical Eng., vol. 102, pp. 141–146, May, 1980.
"Affinity Sensor", Schultz, et al., *Diabetes Care*, vol. 5, No. 3, May–Jun. 1982, pp. 245–253.
"Fiber–Optic Chemical Sensors", Peterson, IEEE/NSF Symposium on Biosensors, 1984, pp. 35–37.
"A Miniature Fiberoptic pH Sensor Potentially Suitable for Glucose Measurements", Peterson et al., *Diabetes Care*, vol. 5, No. 3, May–Jun. 1982, pp. 272–274.
"Optrodes", Borman, *Analytical Chemistry*, vol. 53, No. 14, Dec. 1981, pp. 1616A–1618A.
"Optical Glucose Sensor Based on Reversible Competitive Binding", Mansouri, et al., IEEE/NSF Symposium on Biosensors, 1984.
"A Fiber Optic PCO$_2$ Sensor", Vurek, et al., Annals of Biomedical Engineering, vol. II, pp. 449–510, 1983.
"Fiber–Optic Probe for In Vivo Measurement of Oxygen Partial Pressure", Peterson, et al., *Anal. Chem.*, 56, 1984, pp. 62–67.
"Reusable Glass–Bound pH Indicators", *Anal. Chem.*, vol. 47, No. 2, Feb. 1975, pp. 348–351.
"Fiber–Optic Carbon Dioxodie Partial Pressure Sensor", U.S. Dept. of Commerce NTIS Doc. No. PB83–189738.
"pH Sensor Based on Immobilized Fluoresceinamine", Saari, et al., *Anal. Chem.*, 54, 1982, pp. 821–823.
"Medical Applications of Fiberoptic Sensors", Shultz, *Medical Instrumentation*, vol. 19, No. 4, Jul.–Aug. 1985, pp. 158–163.

*Primary Examiner*—F. L. Evans
*Attorney, Agent, or Firm*—Arnold, White & Durkee

[57] ABSTRACT

A fiber optical probe for colorimetric measurement of chemical properties suitable for the insertion into living tissue. A chemical to be colorimetrically measured is introduced into a sample chamber on the side of the probe near the probe tip. A colorimetric substance contained in the sample chamber changes colors in response to chemical properties of the chemical to be colorimetrically measured, thereby changing the amount of light transmitted through the sample chamber by the optical fibers.

17 Claims, 3 Drawing Figures

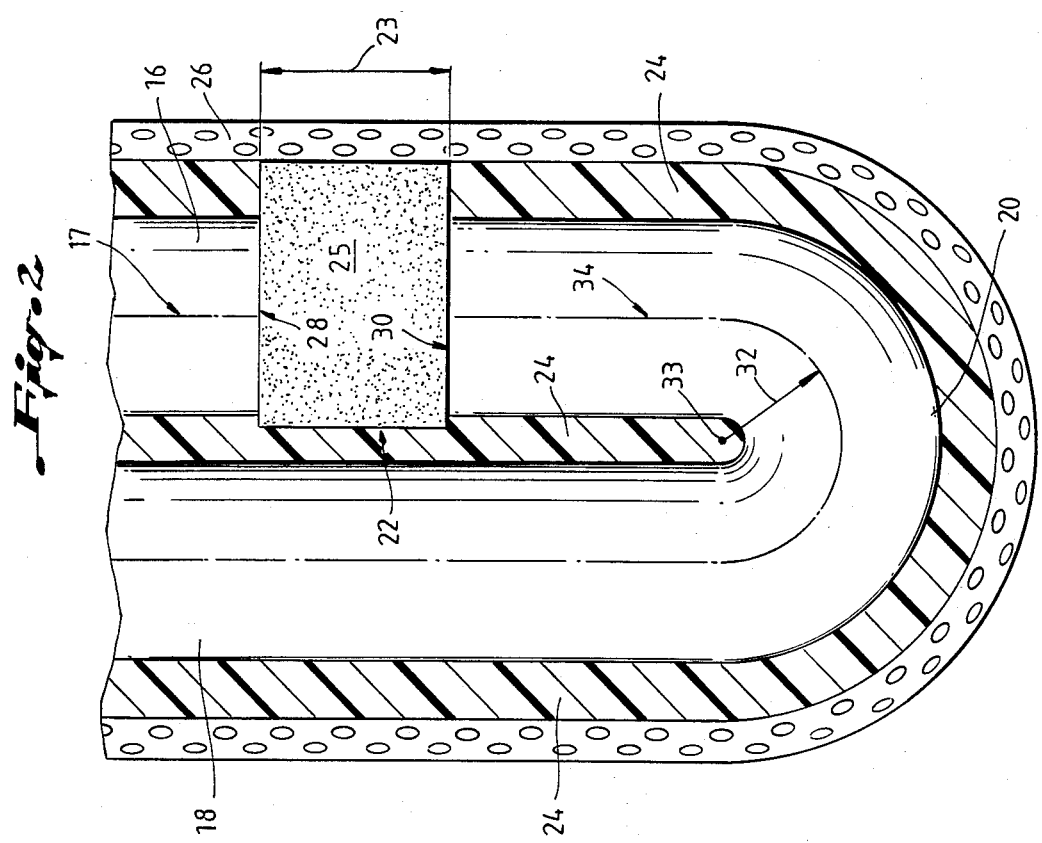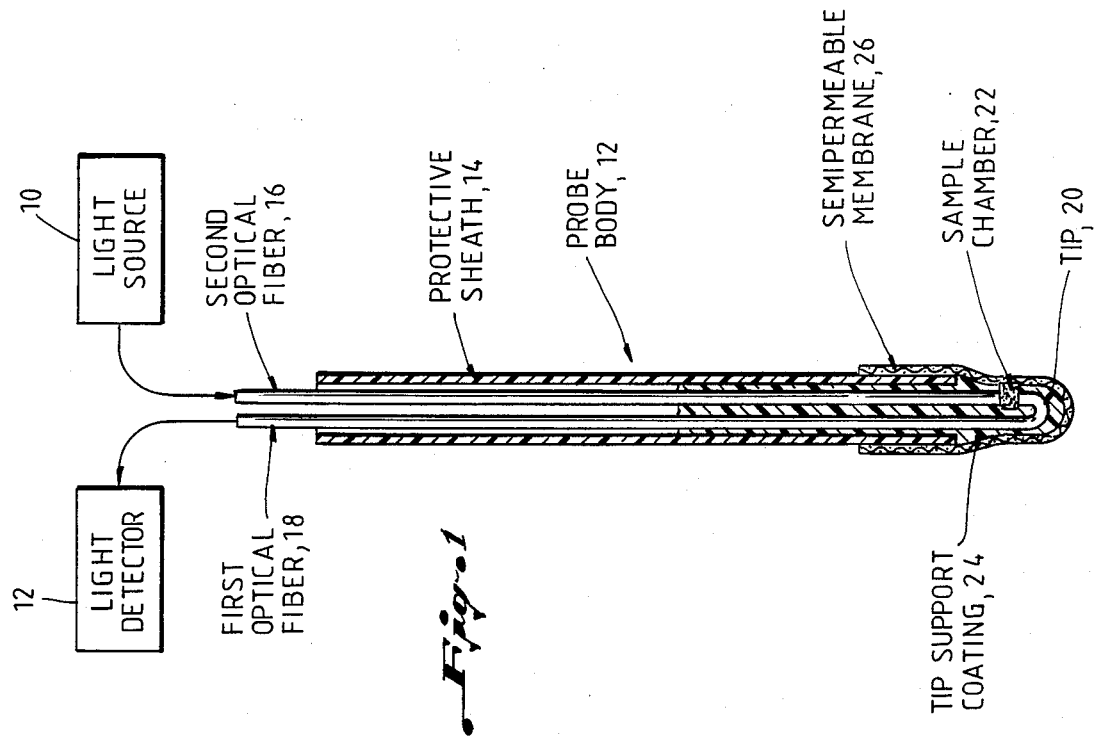

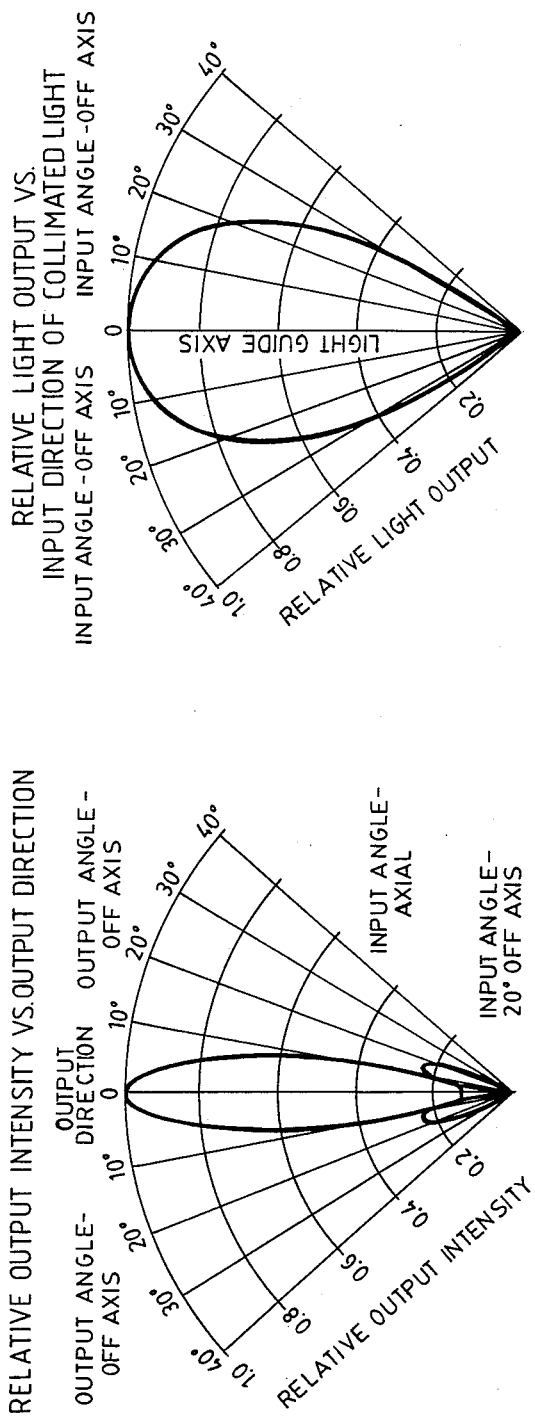
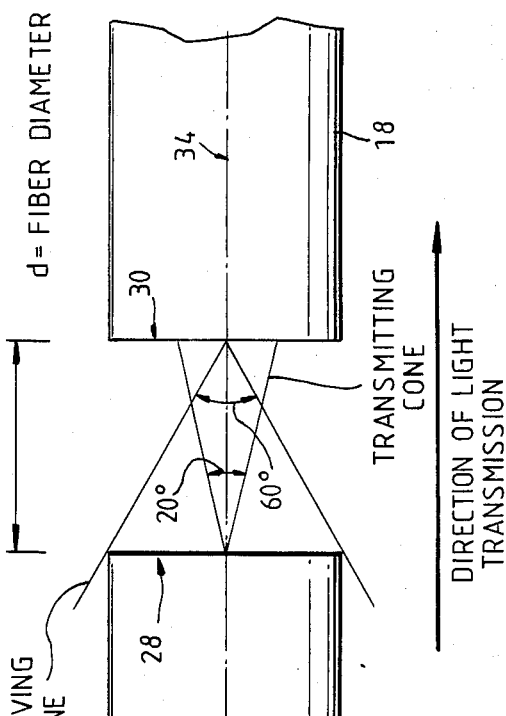
Fig. 3

FIBER OPTIC PROBE FOR QUANTIFICATION OF COLORIMETRIC REACTIONS

BACKGROUND OF THE INVENTION

1. Technical Field

This invention relates to a novel apparatus utilizing fiber optics for colorimetric measurement of chemical properties. More particularly, this invention relates to a fiber optic probe which employs a confronting face optical gap measurement configuration while allowing an overall probe diameter sufficiently small to permit the probe to be inserted into living tissue directly or by prior insertion into a 16-gauge or smaller hypodermic needle.

2. Background Art

Colorimetric measurement of chemical properties is well known in the art. One simple example is the use of a phenophthalein solution which turns red in the presence of a base while becoming clear in the presence of an acid. The use of a colorimetric substance in combination with a fiber optics light source and detector has been taught by many references. Light supplied through a transmitting optical fiber is transmitted through a colorimetric substance mixed with a chemical whose properties are to be measured, and received by a receiving optical fiber which transmits that light to a light detector. A change in color of the colorimetric substance thus changes the light transmissivity of the mixture resulting a different amount of light measured by the light detector. The use of light for the measurement of such quantities as blood pH in vivo is superior to electrical measurement because of the resulting reduced irritation and shock hazard to living tissue. The optical fibers provide a means of channeling the light and making a measurement probe of convenient size.

In prior art configurations, a first optical fiber is connected at one end to a light transmitter and has its opposite end prepared by making a cut at 90° to the axis of the fiber to form a face. A second optical fiber is connected to a light detector at one end and has a face prepared on its opposite end in a manner like that of the first optical fiber.

In one common configuration, the faces of the two optical fibers are arranged so as to confront each other, allowing light from the transmitting fiber to be directed through the chemical to be measured and directly into the face of the receiving optical fiber. The two faces are thus parallel and separated from one another by a distance of typically 0.01 in. so as to form an optical gap. In the simplest configuration of this type, the optical fibers may extend away from the optical gap with their respective axes coincident. A small and more manageable configuration is made by bending the optical fibers so that they may be arranged parallel to one another at a distance away from the optical gap. Such a configuration has been taught in U.S. Pat. No. 3,123,066 by Brumley.

Using the configuration as taught by Brumley, an optical probe may be constructed in which the body consists of two parallel optical fibers suitably fastened together to produce a relatively small diameter probe body. There has been thought to exist a fundamental lower limit to probe tip size, since the respective optical fibers must be bent away from the direction of the probe body direction near the tip and then bent back toward each other to permit the respective faces to closely confront each other at the optical gap. The fundamental lower limit in probe tip size results from the fact that there is a lower limit to the bending radius of the optical fiber. The literature of the fiber optics art teaches that an optical fiber exhibits dramatically reduced transmissivity when bent with a bending radius near that of its outer diameter.

A second configuration has been used which allows a smaller probe tip size. An example of this configuration is disclosed by Peterson, et al., in U.S. Pat. No. 4,200,110. The two optical fibers are arranged parallel to each other along the entire probe length. At the tip, the optical fiber faces are arranged so that they are generally parallel but face the same direction rather than confronting one another. In such a configuration, light is transmitted into the chemical to be measured, thence reflected back to be received at the face of the receiving optical fiber. Light reception then depends upon either the light scattering properties of the chemical to be measured, or upon placement of a reflector at the probe tip. While this second configuration does not require the bending of the optical fibers, it does result in a reduced amount of light available at the face of the receiving optical fiber.

Both configurations have a common disadvantage, in that the measurement chamber is located at the tip of the probe. This limits the sharpness of the probe. Also, there is a greater opportunity for tip breakage if the probe is inserted directly into living tissue. In the prior art, one way of protecting the probe tip has been to insert the probe into a hypodermic needle, and then insert the needle into living tissue. Placement of shielding material at the probe tip interferes with the introduction of the chemical to be colorimetrically measured into the measurement chamber.

SUMMARY OF THE INVENTION

The present invention provides a confronting face optical gap measurement configuration without the attendant large probe tip size disadvantage found in the prior art. In the present invention, a first optical fiber, which may be either the transmitting or receiving fiber, is so constructed to have a sharp, 180° bend placed in it near its face so as to form a hook shape. The face end of the optical fiber is brought back parallel to and closely spaced from the portion of the fiber on the other side of the bend. The bend is referred to as sharp in that the bending radius is smaller than the optical fiber art teaches is possible without unduly reducing the light transmissivity of the fiber. More specifically, a sharp bend in an optical fiber is one in which the bending radius is of the same order of magnitude as the diameter of the optical fiber.

A second optical fiber is laid parallel to the first optical fiber so that its face is parallel to and confronting the face of the first optical fiber. A suitably rigid coating material of epoxy resin or the like, is applied to the two optical fibers to hold the fibers in their respective positions and give the probe structural strength. A sample chamber bored into the protective coating exposes the optical gap and holds the colorimetric substance into which the chemical to be measured is introduced. A semipermeable membrane covers the opening of the sample chamber thereby holding in the colorimetric substance while allowing the chemical to be measured to pass into the sample chamber.

It should be noted that the term semipermeable as applied to membranes admits of two meanings in the relevant literature. An older meaning relates to membranes which allow flow of fluid through them in one direction while preventing flow in the opposite direction. A second meaning of semipermeable as applied to membranes, and the meaning used herein, relates to membranes which allow flow through them substantially equally well in both directions of selected fluids while being substantially equally impervious in both directions to other fluids.

The above description recites the use of two optical fibers, one of which has a tight bend placed in it before probe assembly. In practice, a probe of the type disclosed may be constructed by bending a single optical fiber double in a tight bend and then applying the coating material starting at the tip and moving back along the doubled length of the fiber. When the coating material has dried to form a rigid coating, the sample chamber and optical gap are formed by cutting a slit in the probe. The process of cutting the sample chamber into the tip support coating also results in the severing of the single optical fiber so as to produce the above recited structure containing two optical fibers.

The invention incorporates the advantages of the confronting face optical gap of Brumely while achieving the inherently smaller probe tip size of Peterson, et al. The invention has a further advantage over both the Peterson and Brumley configurations in that the measurement chamber is located on the side of the probe rather than on the tip. The tip thus may be made sufficiently strong and small to permit the probe to be inserted directly into living tissue without being first inserted into a hypodermic needle.

The invention has applications outside the biomedical field in such areas as the food industry. For example, the ruggedness and small size of the probe tip allow insertion into fresh fruit or meat to measure chemical properties therein. Only minimal deformation of the fruit or meat will result from the insertion due to the tip's small size.

BRIEF DESCRIPTION OF THE DRAWINGS

The advantages and features of the invention may be more fully understood from the following description read in conjunction with the accompanying drawings, wherein:

FIG. 1 is a cross-sectional view of the optical probe showing its details of construction and its connection to a light source and detector.

FIG. 2 is an enlarged cross-sectional view of the probe tip showing the details of the sample chamber.

FIG. 3 illustrates the directional properties of the optical fiber as they relate to the determination of the width of the optical gap.

DESCRIPTION OF THE PREFERRED EMBODIMENT

Referring now to FIG. 1, a cross-sectional view of the optical probe may be seen. A probe body 12 is comprised of a first optical fiber 18 and a second optical fiber 16 encapsulated by a protective sheath 14. The protective sheath 14 is preferably a flexible cylindrical tubing approximately 3.5 inches in length made of a material such as teflon. The teflon tubing is thin walled, having an inner diameter of approximately 0.02 inch and a wall thickness of about 0.002 inch. A tip support coating 24 covers the portion of the optical fibers 16 and 18 which protrude about 0.2 inches from one end of the protective sheath 14, and further extends inside the protective sheath 14. A sample chamber 22 opens on the surface of the tip support coating and extends into the interior of the tip support coating 24 for a distance of approximately 0.5 inches.

FIG. 1 shows the optical fibers 16 and 18 spaced apart a distance greater than the diameter of the fibers 16 and 18 primarily to better show the details of construction. Also, considerable space is shown between the inner wall of the protective sheath 14 and the optical fibers 16 and 18, again to better show the construction details. In actual implementation, the protective sheath 14 fits tightly over the optical fibers 16 and 18, so as to force the fibers 16 and 18 to touch each other throughout the interior of the protective sheath 14.

The optical fiber is preferably constructed of polymethyl methacrylate core with an outer covering of transparent polymer of a lower index of refraction than that of the core. A typical outer diameter of the fiber used is about 0.01 inches. Fibers of this type, bundled in groups of up to 64 and covered with a polyethylene resin jacket are sold by Dupont under the registered trademark CROFON. A Dupont 0E0011 optical fiber, not covered by the polyethylene resin jacket, is a suitable fiber for implementation of the present invention.

The tip support coating 24 is preferably an epoxy material which may be applied as a liquid and allowed to dry to a rigid covering. Although FIG. 1 shows the tip support coating 24 to be opaque for clarity, the tip support coating 24 may equally well be transparent or translucent. In addition to providing a rigid protection for the tip 20 and a surrounding medium for the same chamber, the tip support coating helps to anchor the end of the protective sheath 14.

The distal ends of the optical fibers 16 and 18 are optically connected to a light source 10 and a light detector 12 by means of standard and readily available optical couplers, thus permitting the transmission of light through the optical fibers 16 and 18. It should be emphasized that the probe will also function with the light detector 12 connected to the second optical fiber 16 and the light source 10 connected to the first optical fiber 18, allowing the transmission of light in a direction opposite that shown in FIG. 1.

It can be seen that the second optical fiber 16 is arranged parallel and closely spaced from the first optical fiber 18. The first optical fiber 18 extends beyond the proximate end of the second optical fiber 16 and traverses a sharp, 180° bend so that the proximate ends of the optical fibers 16 and 18 confront each other from opposite sides of the sample chamber 22. A tip 20 is formed by the sharp, 180° bend. In practical construction, the optical fibers 16 and 18 would begin as parts of a single optical fiber doubled and drawn through the protective sheath 14, with the tip support coating 24 applied as a liquid. When the tip supporting 24 has hardened, the sample chamber 22 is cut into the hardened tip supporting 24 with the single optical fiber being thus severed to form two separate optical fibers 16 and 18 arranged as shown.

Referring now to FIG. 2, a more detailed view of the optical probe near the tip 20 and sample chamber 22 may be seen. The sharpness of the 180° bend at the tip 20 may be more specifically defined in terms of the bending radius 32 measured from the center of curvature 33 of the bend to the axis 34 of the first optical fiber 18. So as to effect a small tip size, the bending radius is made less than or equal to the diameter of the first optical fiber 18. The fiber optics art teaches that the transmissivity of an optical fiber may drop to 60% or less of its straight line transmissivity when bent with a bending radius this small compared to its diameter. Manufacturers of optical fibers therefore recommend that larger bending radii be used for proper optical fiber operation. The successful operation of the probe while utilizing a bending radius 32 which is less than or equal to the diameter of the first optical fiber 18 is thus a surprising and non-obvious result in view of the prior art teachings.

Proper functioning of the probe with such a small bending radius 32 in contradiction to the accepted understanding in the optical fiber art appears to be based on two factors. First, many applications require optical fiber runs of tens to hundreds of feet in length in which many bends may be required. In such an application, the cumulative reductions in transmissivity caused by long fiber lengths and multiple bends require limitation of losses due to any one bend. The present invention requires a fiber length of the order of 3 feet or less and only one high loss bend. Thus, the high transmissivity loss occasioned by the bend at the tip 20 is not fatal to probe operation.

Secondly, many fiber optics applications involve the transmission of complex waveforms such as that of speech. Small radius bends such as that used in the present invention will cause severe distortion of such complex waveforms. In the present invention, only the amplitude of the light transmitted is measured, so that waveform distortion and resulting unintelligibility of the transmitted light signal is not a factor in probe operation.

Further referring to FIG. 2, details of the sample chamber 22 and the surrounding structure may be seen. The proximate ends of optical fibers 16 and 18 are prepared with faces 28 and 30 respectively. The faces 28 and 30 are flat and are cut so as to be generally perpendicular to the axes of optical fibers 16 and 18 respectively and one thus generally parallel to one another. The faces 28 and 30 are spaced apart to form an optical gap 23. The axis 34, extended beyond face 30 toward face 28, will be seen to be coincident with axis 17.

A maximum width of the optical gap 23 is determined by two factors. First, as the optical gap 23 is increased, less light is received at the receiving face from the transmitting face. Note that in FIG. 2 the face 28 is the transmitting face because the second optical fiber 16 is optically connected to the light source 10. As previously disclosed, the first optical fiber 18 could as well be the fiber optically connected to the light source 10, with the light detector 12 being connected to the second optical fiber 16, thus reversing the transmitting and receiving roles of the faces 28 and 30, respectively.

A second factor affecting the maximum width of the optical gap 23 is the possibility of receiving light at the receiving face 30 from sources other than the transmitting face 28. Referring now to FIG. 3, it can be seen that the faces 28 and 30 are directional in their respective transmitting and receiving functions. Directivity patterns for transmitting and receiving light from the faces of Dupont CROFON optical fibers are shown. Light transmitted from the transmitting face 28 is primarily confined to a transmitting cone of 20° about the axis 17 of the second optical fiber 16. The receiving face 30 takes in light which is primarily confined to a reception cone of 60° about the axis 34 of the first optical fiber 18. If faces 28 and 30 are separated by a distance X greater than $d/2 \tan 30° = 0.868d$, where d is the diameter of the optical fibers, light may be received from ambient sources other than the transmitting face 28, thereby influencing the accuracy of the measurement. Experimentation has shown that examples of the invention having an optical gap 23 of width equal to 1.5 times the diameter of the fibers 16 and 18 are workable but inefficient.

Referring again to FIG. 2, it is seen that the sample chamber 22 is filled with a colorimetric substance 25. The colorimetric substance 25 is such that it is permeable to the chemical to be colorimetrically measured. During the measurement process, the chemical to be colorimetrically measured enters the sample chamber 22 through the semipermeable membrane 26 and permeates the colorimetric substance 25. If the desired property is present in the chemical the colorimetric substance will change color and thus its transmissivity to light will be altered. A change in the intensity of light transmitted from the transmitting face 28 through the sample chamber 22 and received at the receiving face 30 will be detected by the light detector 12, thus signaling the presence of the property sought to be detected.

A colorimetric substance 25 is made by introducing a dye into a porous support medium. One practical embodiment of the porous support medium consists of small glass microspheres with a diameter of approximately 10 micrometers mixed with water to form an aqueous slurry. Irregularly shaped particles with maximum dimensions in the range of 1-100 micrometers may be used in place of the microspheres. Polyurethane particles have also been used although better results have been obtained with glass. The dye is bound to the particles or microspheres before the water is introduced. The addition of water to the particles or microspheres helps to hold the particles or microspheres in place when the semipermeable membrane is applied.

A wide variety of dyes is commercially available in a variety of colors. One example of a dye which has been by some researchers used for the colorimetric measurement of oxygen absorption in the blood is perylene dibutyrate, sold as Thermoplast Brilliant Yellow 10G by BASF-Wyandotte Corporation. The binding of the dye to the support medium may be accomplished by washing the glass particles or microspheres with the dye mixed with an organic solvent such as dichloromethane. A more detailed description of dye selection and the preparation of the porous support medium and dye is presented in the paper entitled "Fiber-Optic Probe for In Vivo Measurement of Oxygen Partial Pressure" by Peterson, Fitzgerald and Buckhold in *Analytical Chemistry*, Vol. 56, No. 1, January, 1984. Harper, in his article entitled "Reusable Glass-Bound pH Indicators" published in Analytical Chemistry, Vol. 47, No. 2, February, 1975, has taught the use of an immobilized subtheilein indicator dye bound to glass fragments for use in pH measurements.

A porous support medium may also be implemented using a solid, porous material such as glass or polyurethane filling the sample chamber. Dye of a suitable type may be imparted into the interstices of the medium and allowed to adhere to the walls thereof. Experimentation has shown the slurry type medium to be somewhat easier to apply to the sample chamber.

The semipermeable membrane 26 is preferably implemented by applying a 2% solution of a cellulose acetate dissolved in a solvent made of 50% acetone and 50% cyclohexanone. The solution is sprayed on as an aerosol after the aqueous slurry is introduced into the sample chamber 22. The aerosol will dry to form a membrane 26 which will serve to hold in the glass particles of the porous support medium while allowing water to flow through the membrane 26.

Increasing the concentration of the cellulose acetate in the solution will result in a smaller pore size in the membrane 26. Extensive literature available on the manufacture of cellulose acetate membranes teaches that concentration of cellulose acetate higher than 2% may be used to produce a membrane permeable to gasses while nonpermeable to water. Such a membrane 26 would be used to hold in the water in the slurry so that a gas to be colorimetrically measured would be dissolved in the water.

The foregoing description of the invention has been directed to a particular preferred embodiment in accordance with the requirements of the patent statute and for purposes of explanation and illustration. It will be apparent, however, to those skilled in this art that many modifications and changes in the embodiments described and illustrated herein may be made without departing from the spirit of the invention.

The following claims are intended to cover such modifications and variations as they fall within the true spirit and scope of the invention.

I claim:

1. An optical probe for colorimetric measurement, comprising:

(a) an optical fiber, having an outer diameter and having light input and output ends for accepting the mounting of optical couplers to enable the transmission of light through said optical fiber, said optical fiber being doubled and having a sharp, 180° bend at a point along its length so as to form a tip, the bend radius of said sharp 180° bend being approximately equal to or less than the outer diameter of said optical fiber, said optical fiber having a small slice extracted from it at a point along its length spaced away from the tip so as to separate said optical fiber into two sections, each section having a face, the respective face of one section linearly displaced from the face of the other section, said displacement of said faces forming an optical gap;

(b) a tip support coating, said tip support coating covering the tip and further extending back along and covering the doubled length of said optical fiber for a distance beyond the optical gap, said tip support coating having a sample chamber which opens on the surface of said tip support coating and which extends into the interior of said tip support coating so as to expose the faces of said optical fiber at the optical gap;

(c) a colorimetric substance, said colorimetric substance filling the sample chamber, said colorimetric substance being permeable to a chemical of which properties are to be colorimetrically measured; and (d) a semipermeable membrane, said semipermeable membrane being applied to the surface of said tip support coating so as to cover the opening of the sample chamber.

2. The optical probe of claim 1, wherein the outer diameter of said optical probe is small enough to permit said optical probe to be inserted into a 16 gauge hypodermic needle.

3. The optical probe of claim 1, wherein the outer diameter of said optical probe is small enough to permit said optical probe to be inserted into a blood vessel.

4. The optical probe of claim 1, wherein said colorimetric substance is comprised of a porous support medium with a dye bound thereto.

5. The optical probe of claim 4, wherein said porous support medium is comprised of a solid porous material with the dye bound to the interstices thereof.

6. The optical probe of claim 4, wherein said porous support medium is comprised of solid particles mixed with a liquid to form a slurry.

7. The optical probe of claim 6, wherein said solid particles are made of glass.

8. The optical probe of claim 6 wherein said solid particles are microspheres.

9. The optical probe of claim 6, wherein said liquid is water.

10. An optical probe for colorimetric measurement, comprising:

(a) a first optical fiber having a distal end prepared to accept an optical coupler and a proximate end having a face, said first optical fiber having a 180° bend near its proximate end to form a tip, with bending radius being less than or equal to the diameter of said first optical fiber;

(b) a second optical fiber having a distal end prepared to accept an optical coupler and a proximate end having a face, said second optical fiber being placed closely to and running parallel to said first optical fiber so that the proximate end face of said first optical fiber confronts the proximate end face of said second optical fiber to form an optical gap;

(c) a flexible protective sheath surrounding said optical fibers, the respective proximate ends of said optical fibers protruding from the proximate end of said flexible protective sheath so as to leave the tip and the optical gap exposed, the distal ends of said optical fibers protruding from the distal end of said flexible protective sheath;

(d) a rigid tip support coating covering that part of the proximate ends of said optical fibers exposed by said protective sheath and further extending inside and filling the interior of said protective sheath near the proximate end of said protective sheath, said tip support coating having a sample chamber opening on the surface of said tip support coating and extending inward into said tip support coating and the optical gap so as to expose the proximate end faces of said optical fibers;

(e) a colorimetric substance filling said sample chamber, said colorimetric substance comprised of glass fragments with a dye bound thereto, the fragments being mixed with water to form a slurry; and (f) a semipermeable membrane applied to the surface of said tip support coating so as to cover the opening of the sample chamber, said semipermeable membrane extending back along said optical probe so as to cover a portion of said protective sheath, said semipermeable membrane being chosen so as to allow the flow of a selected chemical to be colorimetrically measured while prohibiting the flow of other chemicals.

11. An optical probe for colorimetric measurement, comprising:

(a) a first optical fiber having a distal end for engagement to an optical coupler and a proximate end having a cross-sectional surface, said first optical fiber having a substantially 180° bend near its proximate end forming a tip;

(b) a second optical fiber having a distal end for engagement to an optical coupler and a proximate end having a cross-sectional surface, said second optical fiber aligned substantially parallel to said first optical fiber such that the proximate cross-sectional surface of said first optical fiber faces the proximate cross-sectional surface of said second optical fiber forming an optical gap, said first optical fiber and said second optical fiber having outer diameters, the shortest distance between the part of the first optical fiber on one side of said bend and the part of the first optical fiber on the opposite side of the bend being less than or approximately equal to the outer diameter of said first optical fiber;

(c) a tip support coating, said tip support coating covering the tip of said first optical fiber;

(d) a semipermable membrane, said semipermeable membrane covering the opening of said optical gap to form a sample chamber.

12. The optical probe of claim 11, further including a flexible protective sheath encapsulating said optical fibers, said sheath engaging said tip support coating.

13. The optical probe of claim 11, further including a colorimetric substance, said colorimetric substance filling the sample chamber, said colorimetric substance permeable to a chemical having properties that may be colorimetrically measured.

14. The optical probe of claim 11, wherein said tip support coating extends along said probe until covering both first and second optical fibers for a distance beyond said optical gap, said tip support coating encapsulating said sample chamber which opens on the surface of said tip support coating and which extends into the interior of said tip support coating exposing the cross-sectional surfaces of said first and second optical fibers.

15. The optical probe of claim 11, further including a protective sheath, encapsulating said optical fiber, engaged to said tip support coating, and whrein said semipermeable membrane covers the opening of said sample chamber and extends along said optical probe so as to cover a portion of said protective sheath.

16. The optical probe of claim 11 wherein the length of said optical gap is approximately equal to or less than 1.5 times the length of the outer dimaeter of said first optical fiber.

17. The optical probe of claim 11 wherein the length of said optical gap is approximastely equal to or less than the outer diameter of said first optical fiber.

* * * * *